(12) United States Patent
Meguro et al.

(10) Patent No.: US 7,150,723 B2
(45) Date of Patent: Dec. 19, 2006

(54) MEDICAL DEVICE INCLUDING GUIDE WIRE AND BALLOON CATHETER FOR CURING A CORONARY ARTERY

(75) Inventors: Taiichiroh Meguro, Sendai (JP); Masashi Momota, Nagoya (JP); Tomihisa Kato, Nagoya (JP)

(73) Assignees: C-I-Medic Co., Ltd., Miyagi-ken (JP); Asahi Intecc Co., Ltd., Aichi-ken (JP)

( * ) Notice: Subject to any disclaimer, the term of this patent is extended or adjusted under 35 U.S.C. 154(b) by 0 days.

(21) Appl. No.: 11/146,143

(22) Filed: Jun. 7, 2005

(65) Prior Publication Data

US 2005/0228431 A1    Oct. 13, 2005

Related U.S. Application Data

(63) Continuation-in-part of application No. 09/995,789, filed on Nov. 29, 2001, now abandoned.

(51) Int. Cl.
*A61M 25/00* (2006.01)
*A61M 5/178* (2006.01)
*A61M 29/00* (2006.01)
*A61B 5/00* (2006.01)

(52) U.S. Cl. .............. 604/96.01; 604/164.13; 600/585

(58) Field of Classification Search ........ 600/433, 600/434, 435, 585; 604/95.01, 96.01, 103.03, 604/103.09, 164.01, 164.03, 164.13, 165.01, 604/165.02, 170.01, 170.02, 523, 524, 526, 604/528

See application file for complete search history.

(56) References Cited

U.S. PATENT DOCUMENTS

| | | | |
|---|---|---|---|
| 4,413,989 A * | 11/1983 | Schjeldahl et al. | 604/103.13 |
| 4,616,653 A * | 10/1986 | Samson et al. | 606/192 |
| 5,368,048 A * | 11/1994 | Stoy et al. | 600/585 |
| 5,378,236 A * | 1/1995 | Seifert | 604/99.04 |
| 5,409,470 A * | 4/1995 | McIntyre et al. | 604/528 |
| 5,454,788 A * | 10/1995 | Walker et al. | 604/99.04 |
| 5,465,733 A * | 11/1995 | Hinohara et al. | 600/585 |
| 5,766,192 A * | 6/1998 | Zecca | 606/159 |
| 6,132,389 A * | 10/2000 | Cornish et al. | 600/585 |
| 6,416,526 B1 * | 7/2002 | Wyzgala et al. | 606/170 |

\* cited by examiner

*Primary Examiner*—Max F. Hindenburg
*Assistant Examiner*—Jonathan Foreman
(74) *Attorney, Agent, or Firm*—Morgan, Lewis & Bockius LLP

(57) ABSTRACT

In a medical guide wire 1, a rear half of a leading bulge portion (ellipsoidal helical spring) 5 forms a truncated cone shaped front catheter engagement portion 8. An inner wall of a balloon catheter 2 forms a flared end portion 2A which absorbably fits into the front catheter engagement portion 8 due to the physical adhesion so to provisionally connect the balloon catheter 2 to the front catheter engagement portion 8. The medical guide wire 1 and the balloon catheter 2 are inserted into the blood vessel with one single step procedure when the medical guide wire 1 is introduced into the blood vessel to place the balloon portion 10 at the stricture blood vessel area (P).

2 Claims, 11 Drawing Sheets

MEDICAL DEVICE INCLUDING GUIDE WIRE AND BALLOON CATHETER FOR CURING A CORONARY ARTERY

The present application is a continuation-in-part of U.S. patent application Ser. No. 09/995,789, filed Nov. 29, 2001 now abandoned.

BACKGROUND OF THE INVENTION

1. Field of the Invention

The invention relates to a medical device including a guide wire used at the time when a balloon catheter is placed at a strictured area of a blood vessel (e.g., coronary artery) to cure the strictured area, and particularly concerns to a balloon catheter used in combination with the medical guide wire.

2. Description of Related Art

Upon treating a strictured area of a blood vessel, a very thin flexible medical guide wire is inserted into the strictured area of the blood vessel to place a leading end of the guide wire to advance past the strictured area.

Thereafter, a tubular balloon catheter is introduced along the guide wire to reach the strictured area by handling a grip of the guide wire outside the blood vessel.

Then, a balloon portion of balloon catheter is inflated due to a liquid (e.g., physiological saline solution) infused into the balloon catheter to forcibly expand the strictured area of the blood vessel. This permits a normal amount of blood to run through the strictured area of the blood vessel so as to remedy the strictured area of the blood vessel. By way of illustration, this is exemplified by a Japanese Provisional Utility Model Publication No. 5-19078.

In the prior remedial method in which the medical guide wire is inserted into the blood vessel, and thereafter the balloon catheter is introduced along the guide wire into the strictured area of the blood vessel, two step procedures are required to inflate the balloon portion. One is inserting the guide wire, and the other is introducing the balloon catheter into the strictured area of the blood vessel along the guide wire. To implement the two step procedures would be time-consuming, and aggravate pains that the patient sustains, in addition to intrusiveness that the patient feels, during the manipulation of the medical guide wire against the blood vessel.

Further, in the case in which the medical guide wire is absorbably capped with the balloon catheter that is diametrically greater than the medical guide wire, an open edge of the balloon catheter forms a stepped section against the medical guide wire.

The stepped section would become an obstacle upon inserting the guide wire into the strictured area of the blood vessel. This is all the more time-consuming because the manipulator must be prudent not to make the stepped section hitch the strictured area and the blood vessel. Otherwise, the stepped section would injure the blood vessel and/or the strictured area of the blood vessel.

Therefore, the present invention has been made with the above drawbacks in mind, it is a main object of the invention to provide a medical guide wire for curing a coronary artery combined with a balloon catheter which is capable of inserting the medical guide wire into a blood vessel and a strictured area of the blood vessel smoothly and quickly without injuring them, thus achieving remedial procedures for a short period of time with ease and safety.

SUMMARY OF THE INVENTION

According to the present invention, there is provided a medical guide wire having an elongated and flexible core member, a front catheter engagement portion provided around the core member and formed into a bulged shape or a truncated cone shape, a diameter of which progressively decreases as approaching a rear end of the front catheter engagement portion. The front catheter engagement portion is capped with the balloon catheter to provisionally connect the balloon catheter to the front catheter engagement portion so that the balloon catheter is introduced into a blood vessel together with the medical guide wire.

According to other aspect of the invention, a provisionally connecting member is provided at a front open end of the balloon catheter to provisionally connect the balloon catheter to the front catheter engagement portion.

The provisionally connecting member is a carve in the form of kerf, slot, notch or slit defined at the front open end of the balloon catheter. Otherwise, the provisionally connecting member is a rolled end or a spiral groove which fit into the leading bulge portion formed by the ellipsoidal helical spring.

According to other aspect of the invention, the balloon catheter and the front catheter engagement portion are formed by a common synthetic resin to produce a coefficient of static friction therebetween, a magnitude of which is determined enough to provisionally connect the balloon catheter to the front catheter engagement portion.

With the medical guide wire capped with the balloon catheter assembled before introducing into the blood vessel, the assemble of the medical guide wire and the balloon catheter act as a leading head portion to guide the guide wire into the blood vessel. By concurrently inserting the medical guide wire and the balloon catheter into the blood vessel, it is possible to place a balloon portion of the balloon catheter at the stricture blood vessel area with one single step procedure.

After inflating the balloon portion at the stricture blood vessel area, it is necessary to withdraw the balloon catheter from the medical guide wire to replace the balloon portion in turn with larger ones. For this purpose, the provisionally connecting member is provided to separate the balloon catheter from the medical guide wire by simply pulling a rear end of the balloon catheter exposed outside the blood vessel.

The front catheter engagement portion is in integral with the leading bulge portion to readily introduce the leading bulge portion into the stricture blood vessel area.

As other alternatives, the front catheter engagement portion is connected in series with the leading bulge portion, and connected to the leading bulge portion by means of a soldering or an adhesive.

As the provisionally connecting member, the front catheter engagement portion and the balloon catheter are formed by the common synthetic resin to determine the coefficient of the static friction therebetween, a magnitude of which is great enough to provisionally connect the balloon catheter to the front catheter engagement portion.

With the medical guide wire thus combined with the balloon catheter, it is possible to concurrently introduce the balloon catheter and the medical guide wire into the stricture blood vessel area at the time when leading the medical guide wire into the stricture blood vessel area.

This enables a manipulator to attain the balloon catheter to the stricture blood vessel area with one single step procedure so as to quickly prepare for the treatment more than the prior art which requires the two step procedures to lead the balloon catheter into the stricture blood vessel area.

With the use of the provisionally connecting member, it is possible to smoothly advance the guide wire into the sinuous blood vessel without slipping the balloon catheter off the guide wire, and further replacing the balloon catheter readily with larger ones.

With the front catheter engagement portion leading the balloon catheter into the strictured area of the blood vessel, it is possible to prevent the blood vessel and the strictured area of the blood vessel from getting injured due to the presence of the front open edge of the balloon catheter. This also facilitates to place the balloon catheter at the strictured area of the blood vessel safely with ease.

BRIEF DESCRIPTION OF THE DRAWINGS

A preferred form of the present invention is illustrated in the accompanying drawings in which.

DETAILED DESCRIPTION OF THE PREFERRED EMBODIMENTS

Figure 1:
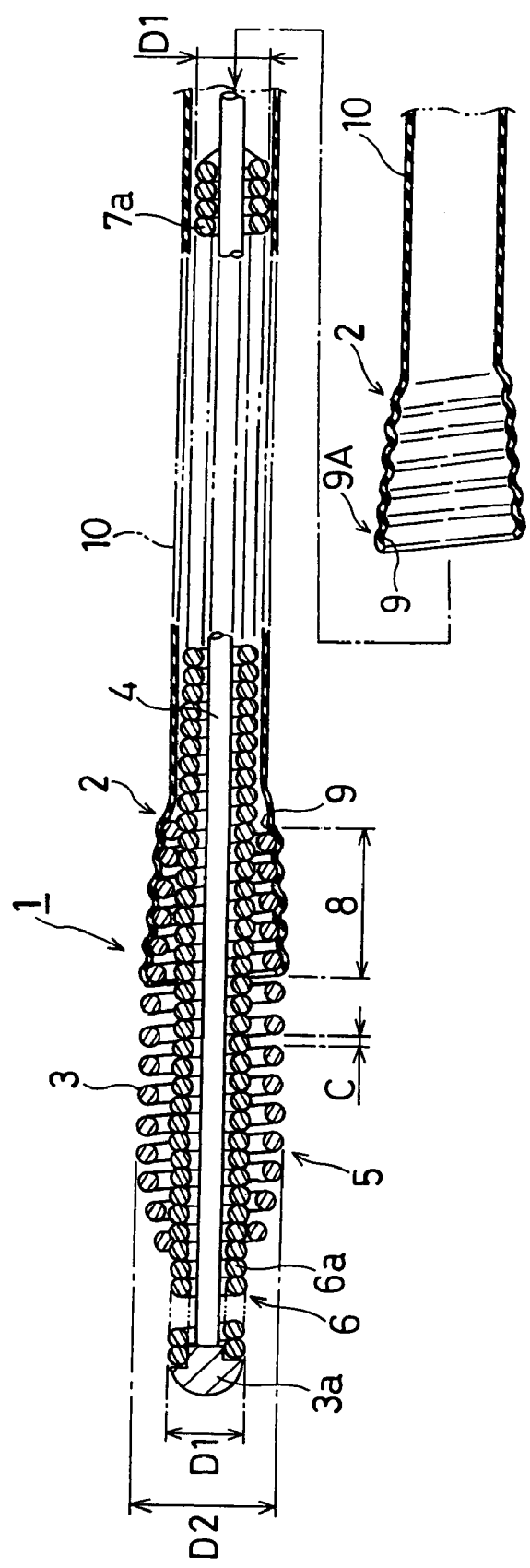
FIG. 1 is a longitudinal cross sectional view of a medical guide wire and a balloon catheter according to a first embodiment of the invention.
Figure 2:
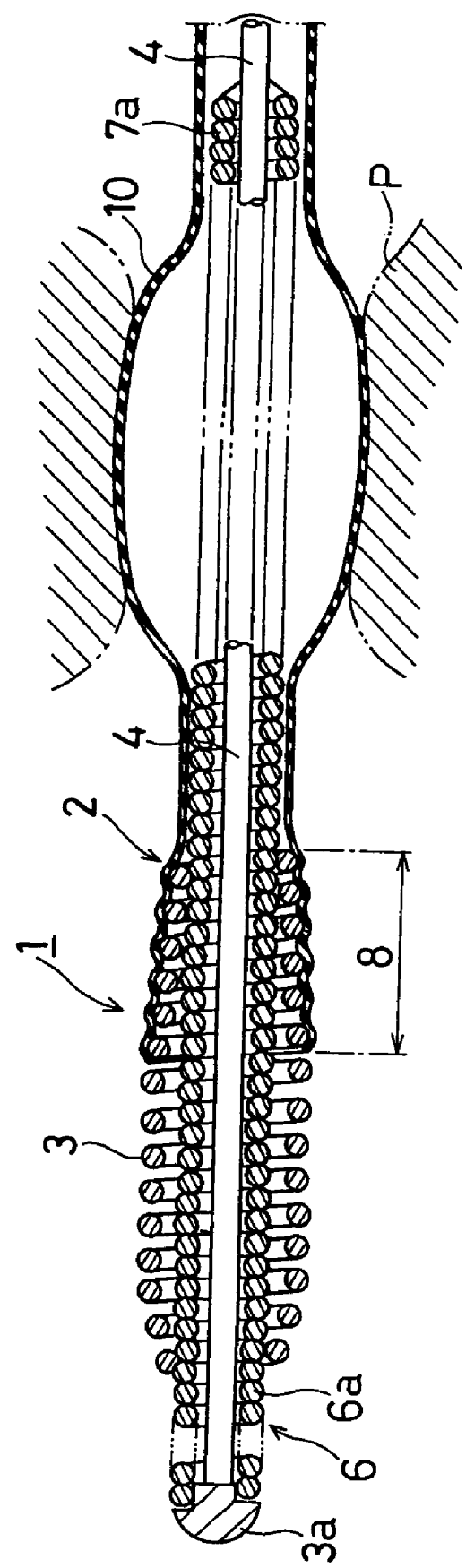
FIG. 2 is a longitudinal cross sectional view of the medical guide wire combined with the balloon catheter.

Referring to FIGS. 1 and 2 which show a medical guide wire 1 and a tubular balloon catheter 2 used to the medical guide wire 1 according to a first embodiment of the invention, a helical spring 6 is coiled around an elongated and flexible core member 4, a front end of which has a head portion 3a.

The helical spring 6 has a diameter (D1) which is greater than that of the core member 4, and has coil line elements tightly arranged along the core member 4 with no clearance appeared between the coil line elements.

Around a front portion of the helical spring 6, an ellipsoidal helical spring 3 is provided to form a leading bulge portion 5. The ellipsoidal helical spring 3 has a maximum diameter (D2), a rear half of which forms a front catheter engagement portion 8 shaped into a truncated cone configuration, a diameter of which progressively decreases as approaching a rear end of the front catheter engagement portion 8.

The leading bulge portion 5 acts as a soft and flexible guide member effective when the medical guide wire 1 is inserted into a strictured area (P) of a blood vessel. (e.g., coronary artery).

In the leading bulge portion 5, the ellipsoidal helical spring 3 is fixed to the helical spring 6 by means of a soldering or an adhesive. The helical spring 6 has a forward portion 6a and a rearward portion 7a each connected consecutively along the core member 4. The ellipsoidal helical spring 3 has coil line elements arranged over the helical spring 6 with a certain clearance (C) appeared between the coil line elements. The ellipsoidal helical spring 3 forms the front catheter engagement portion 8 extending from the section of the maximum diameter (D2) to a boundary area in which the section of the maximum diameter (D2) start to descend to the thin helical spring section of the diameter (D1).

The balloon catheter 2 is formed by a flexible synthetic resin, and an outer wall of the balloon catheter 2 has a spiral groove 9 to serve as a connecting member 9A. By pushing an open front end of the balloon catheter 2 against the front catheter engagement portion 8, the spiral groove 9 slip-fits into the coil line elements of the ellipsoidal helical spring 3 to provisionally (detachably) connect the balloon catheter 2 to the front catheter engagement portion 8.

Upon inserting the medical guide wire 1 into a blood vessel, the leading bulge portion 5 advances into the blood vessel together with the balloon catheter 2 to place a balloon portion 10 at the strictured area (P) of the blood vessel.

Figure 3:
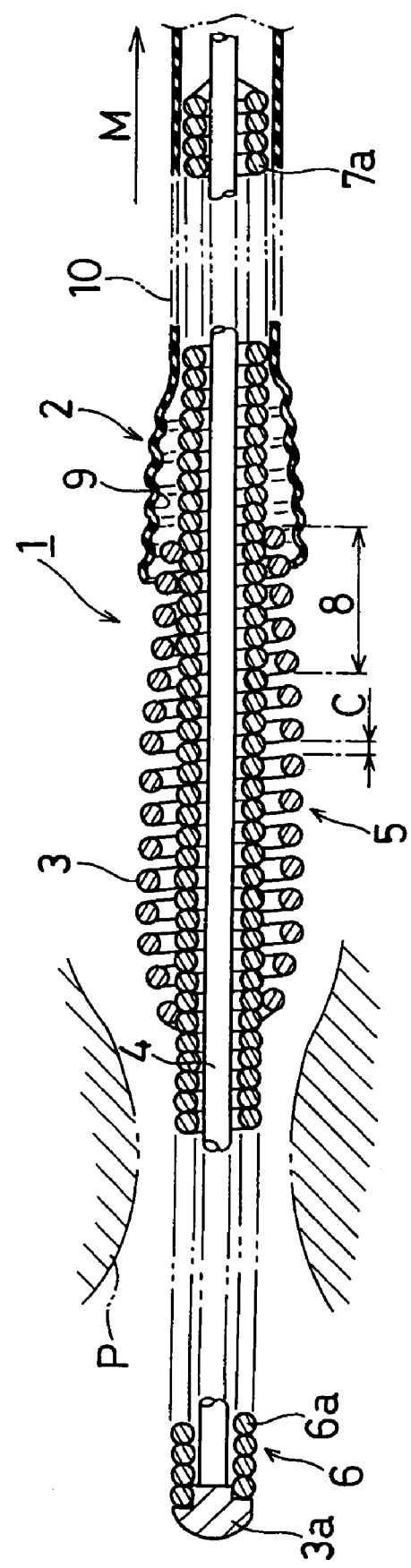
FIG. 3 is a longitudinal cross sectional view shown to explain how to manipulate the medical guide wire.

Then, a physiological liquid is injected into the balloon portion 10 to inflate it so as to expand the strictured area (P) of the blood vessel as shown in FIG. 2. When the balloon portion 10 is replaced with a larger one, the balloon catheter 2 is pulled in the direction of an arrow M to such a degree as to move the leading bulge portion 5 behind the strictured area (P) of the blood vessel as shown in FIG. 3. By fully pulling a rear grip handle (not shown) being manipulated outside the blood vessel, the balloon catheter 2 separates from the leading bulge portion 5 so as to be withdrawn from the leading bulge portion 5.

When the balloon portion 10 is replaced by a still larger one, a diameter-increased balloon catheter is introduced along the medical guide wire 1 into the blood vessel to provisionally connect the balloon catheter 2 to the front catheter engagement portion 8 so as to lead the new balloon portion into the strictured area (P) of the blood vessel. Thus, the balloon portion 10 is replaced in turn by still larger ones.

It is to be noted that the spiral groove 9 is formed by forcibly fitting the heated balloon catheter 2 into the front catheter engagement portion 8.

In this instance, the front catheter engagement portion 8 approximately measures 0.56 mm in maximum diameter, 0.355 mm in minimum diameter and 2.0 mm in length. The forward portion 6a of the helical spring 6 approximately measures 40.0 mm in length, the leading bulge portion 5 approximately measures 5.0 mm in length, and the helical spring 6 approximately measures 300 mm in length.

With the structure thus described, it is possible to insert the medical guide wire 1 into the blood vessel in combination with the balloon catheter 2. In addition, the front catheter engagement portion 8 is formed in integral with the leading bulge portion 5. This eliminates the necessity of providing a discrete front catheter engagement portion, thus conducing to simplifying a whole structure with a lower cost.

With the clearance (C) appeared between the coil line elements of the ellipsoidal helical spring 3, the clearance (C) admits blood streams running through the strictured area (P) of the blood vessel when the leading bulge portion 5 is placed at the strictured area (P) of the blood vessel.

Under the presence of the clearance (C), it is possible to determine a greater lead pitch between the coil line elements of the ellipsoidal helical spring 3. The greater lead pitch enables a manipulator to a longer travel when the leading bulge portion 5 is rotated to advance the leading bulge portion 5 past the strictured area (p) of the blood vessel with the ellipsoidal helical spring 3 engaged against an inner wall of the strictured area (P) of the blood vessel. This quickly advances the leading bulge portion 5 to easily place the balloon portion 10 at the strictured area (P) of the blood vessel.

By moving the leading bulge portion 5 back and forth through the strictured area (P), remnants deposited on the inner wall of the strictured area (P) are partly removed to open the strictured area (P) wider. The widely opened strictured area (P) makes it easier to introduce the balloon portion 10 into the strictured area (P), thus conducing to smoothly placing the balloon portion 10 at the strictured area (P) safely with ease.

When a stent already retained in the strictured area (P) is abnormally deformed, the medical guide wire 1 can be introduced together with the balloon catheter 2 into the blood vessel to treat the strictured area (P) of the blood vessel. The leading bulge portion 5 moves into the stent to gradually rectify the deformed stent so as to facilitate the treatment appropriately as opposed to the prior art in which the balloon catheter may hitch the deformed stent to block its passage going through the strictured area (P) of the blood vessel.

Figure 4:
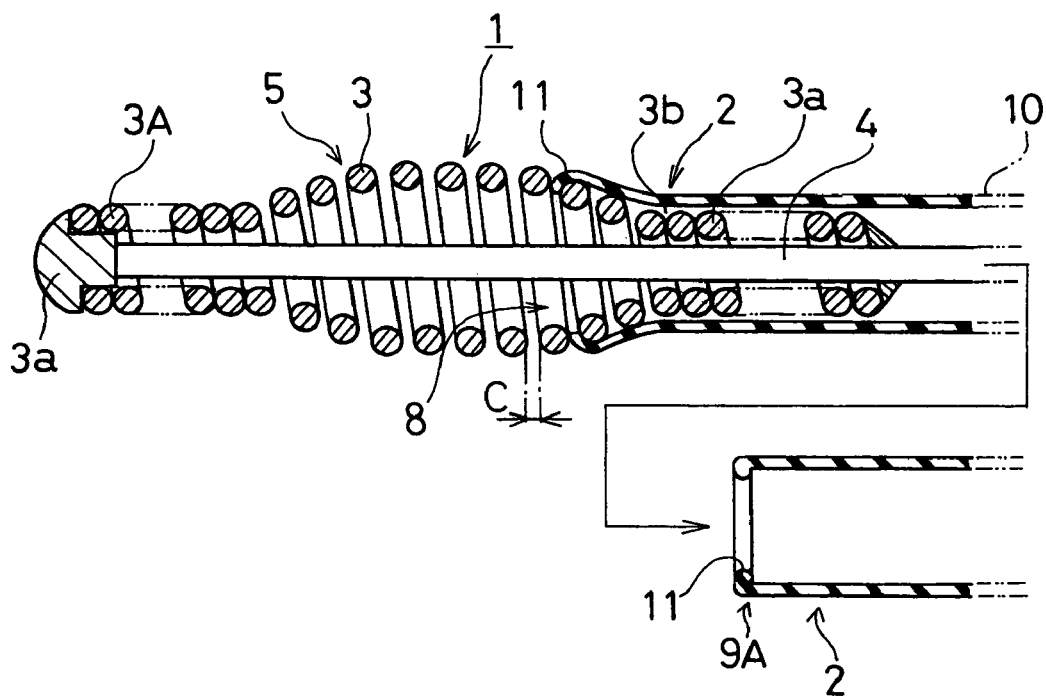
FIG. 4 is a longitudinal cross sectional view of the medical guide wire combined with the balloon catheter according to a second embodiment of the invention.

FIG. 4 shows a second embodiment of the invention in which the provisionally connecting member 9A is formed on an open front end of the balloon catheter 2.

The open front end of the balloon catheter 2 is rolled inward to define a rolled end 11. The rolled end 11 is placed at the clearance (C) to fit the coil line element of the ellipsoidal helical spring 3 which is positioned between a diameter-reduced forward helical spring 3A and a diameter-reduced rearward helical spring 3B to provisionally connect the balloon catheter 2 to the front catheter engagement portion 8.

Instead of placing the rolled end 11 at the clearance (C), the rolled end 11 can fit into a helical cavity 3b formed between the tightly arranged coil line elements of a diameter-reduced reward helical spring 3B to provisionally connect the balloon catheter 2 to the front catheter engagement portion 8.

Due to the absence of an outwardly directed edge usually defined on the open front end of the balloon catheter 2 and detrimental to the blood vessel when inserting the balloon catheter 2 into the blood vessel, the medical guide wire 1 can be safely inserted into the blood vessel together with the balloon catheter 2.

Considering that the rolled end 11 is formed by pushing the open front end of the heated balloon catheter 2 against a die mold before cooling down the balloon catheter 2, a molecular orientation caused by rolling a crystallized resin hypotube is tempered to alleviate the mechanical anisotropy. This allows the rolled end 11 to restore the appropriate flexibility so as to render the provisionally connecting member 9A functionally effective.

Figure 5:
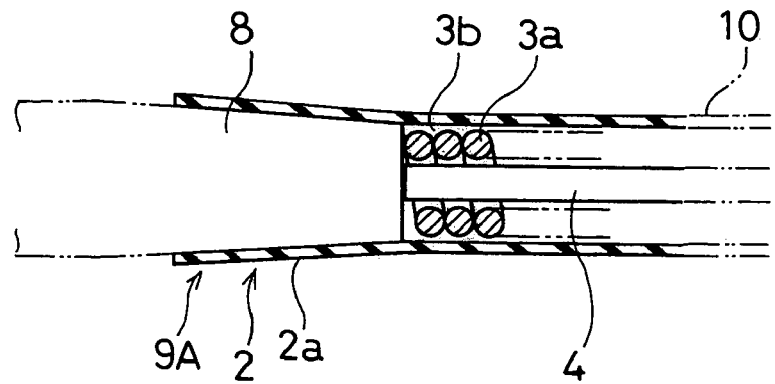
FIG. 5 is a longitudinal cross sectional view of the medical guide wire capped with the balloon catheter according to a third embodiment of the invention.

FIG. 5 shows a third embodiment of the invention in which the front catheter engagement portion 8 is in the form of a truncated cone configuration, a diameter of which progressively decreases as approaching the helical spring 3a wound around the core member 4.

The front catheter engagement portion 8 and the balloon catheter 2 are formed commonly by a polyamide-based synthetic resin. For example, the balloon catheter 2 is formed by polyamide, and the front catheter engagement portion 8 by polyimide or hot melt adhesive (a.k.a. Bestamelt Adhesive as a Trade Name). A front section 2a of the balloon catheter 2 is forcibly fit over the front catheter engagement portion 8 to provisionally connect the balloon catheter 2 to the front catheter engagement portion 8 to serve as the provisionally connecting member 9A.

For this reason, a coefficient of static friction between the front section 2a of the balloon catheter 2 and the front catheter engagement portion 8 is determined to be such a magnitude as to provisionally connect the balloon catheter 2 to the front catheter engagement portion 8.

In this instance, at least the front section 2a of the balloon catheter 2 and the front catheter engagement portion 8 are preferably formed by polyamide, polyvinyl chloride, polytetrafluoroethylene or polyethylene.

As an alternative, a mirror-finish treatment is provided with an outer surface of the front catheter engagement portion 8 formed into the truncated cone configuration, so as to make the front catheter engagement portion 8 act as a mirror-finished barrel portion which is to absorbably engages with the front section 2a of the balloon catheter 2. Since an outer surface of the front catheter engagement portion 8 forms an entirely mirrored surface, and absorbably enages with the front section 2a of the balloon catheter 2 due to a physical adhesion, applying a withdrawing force makes it possible to easily disconnect front catheter engagement portion 8 from the balloon catheter 2.

Figure 6:
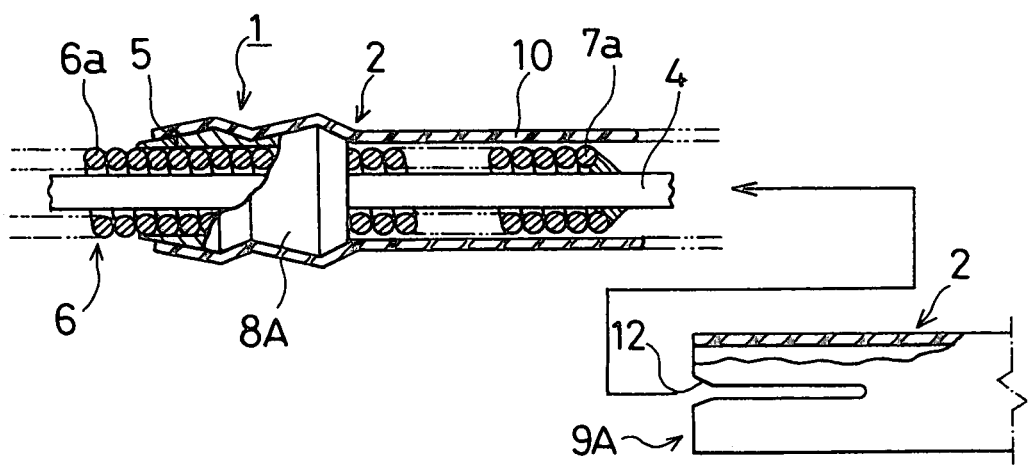
FIG. 6 is a longitudinal cross sectional view of the medical guide wire combined with the balloon catheter according to a fourth embodiment of the invention.

FIG. 6 shows a fourth embodiment of the invention in which a front catheter engagement portion 8A is formed around the helical spring 6 into a gourd-shaped (columnar-shaped) configuration. The front catheter engagement portion 8A is mirror-finished after molding it from the hot melt adhesive based on polyamide, polyethylene or the like (thermally sensitive adhesive) or silicone-based adhesive (reactive type adhesive).

An open end section of the balloon catheter 2 has a pair of diametrically opposed axial carves 12 in the form of a kerf, slit, slot or notch. The axial carves 12 help expand the balloon catheter 2 when fitting the balloon catheter 2 over the front catheter engagement portion 8A to provisionally connect the two members.

The adhesive materials makes it possible to soften the front catheter engagement portion 8A to render it more flexible, which is experienced when the medical guide wire 1 is manipulated. The mirror-finish treatment renders the balloon catheter 2 to tightly attach to the front catheter engagement portion 8A so as stabilize the function of the provisionally connecting member 9A.

Figure 7:
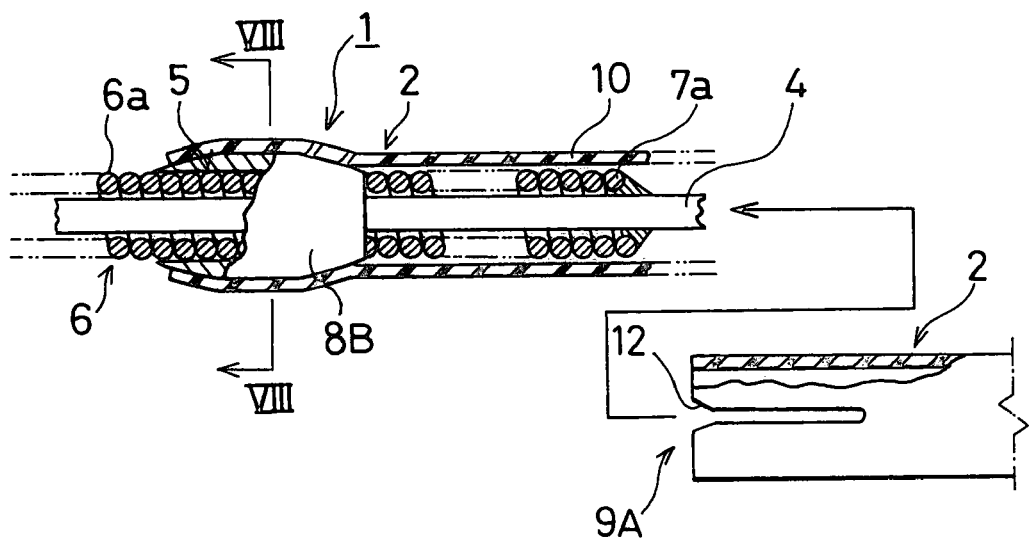
FIG. 7 is a longitudinal cross sectional view of the medical guide wire combined with the balloon catheter according to a fifth embodiment of the invention.
Figure 8:
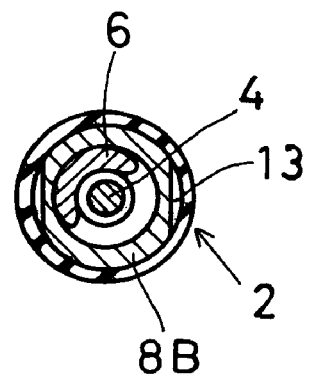
FIG. 8 is a latitudinal cross sectional view taken along the line VIII—VIII of FIG. 7.

FIGS. 7 and 8 show a fifth embodiment of the invention which differs from the fourth embodiment in that a front catheter engagement portion 8B is formed into a barrel-shaped (columnar-shaped) configuration. With lengthwise sides of the front catheter engagement portion 8B, is a flat section 13 provided.

It is to be noted that the carves 21 are not always necessary, and the carves 21 may be omitted depending on the configuration of the front catheter engagement portion 8A (8B). Instead of using the adhesive materials to the front catheter engagement portion 8A (8B), an annular tube may be soldered around the helical spring 6 to form the front catheter engagement portion. Otherwise, the front catheter engagement portion may be formed by depositing multi-layered solder on the helical spring 6.

Figure 9:
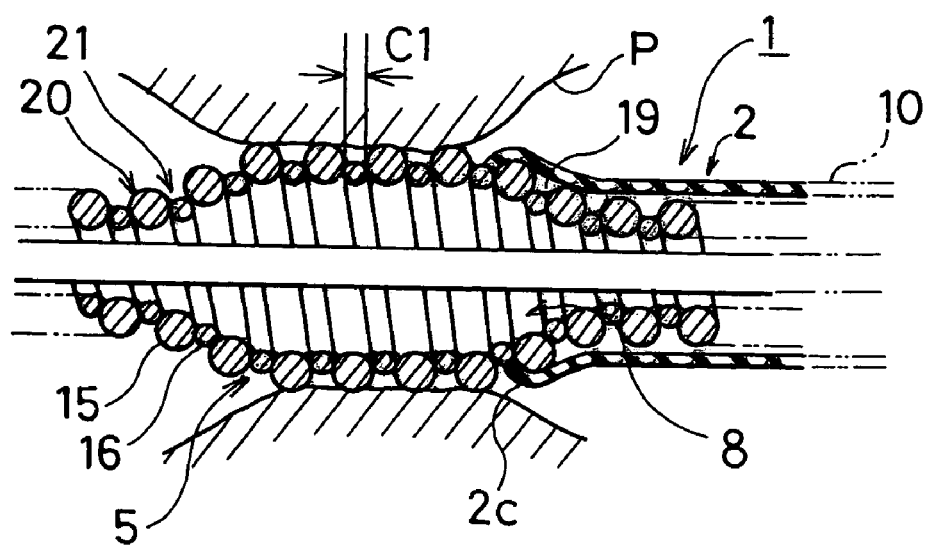
FIG. 9 is a longitudinal cross sectional view of the medical guide wire combined with the balloon catheter according to a sixth embodiment of the invention.

FIG. 9 shows a sixth embodiment of the invention in which the leading bulge portion 5 forms a composite helical spring structure combining a first ellipsoidal helical spring 20 with a second ellipsoidal helical spring 21. Line coil elements 15 of the first ellipsoidal helical spring 20 is diametrically greater than coil line elements 16 of the second ellipsoidal helical spring 21.

The former coil line elements 15 and the latter coil line elements 16 are alternately arranged tightly with no clearance provided between their neighboring coil line elements. A rear half section of the leading bulge portion 5 defines the front catheter engagement portion 8.

Upon provisionally connecting the balloon catheter 2 to the front catheter engagement portion 8, an open end section 2c of the balloon catheter 2 is elastically expanded so that the open end section 2c fits into a helical cavity 19 (i.e., clearance C1) formed between the coil line elements 15 of the first ellipsoidal helical spring 20.

Figure 10:
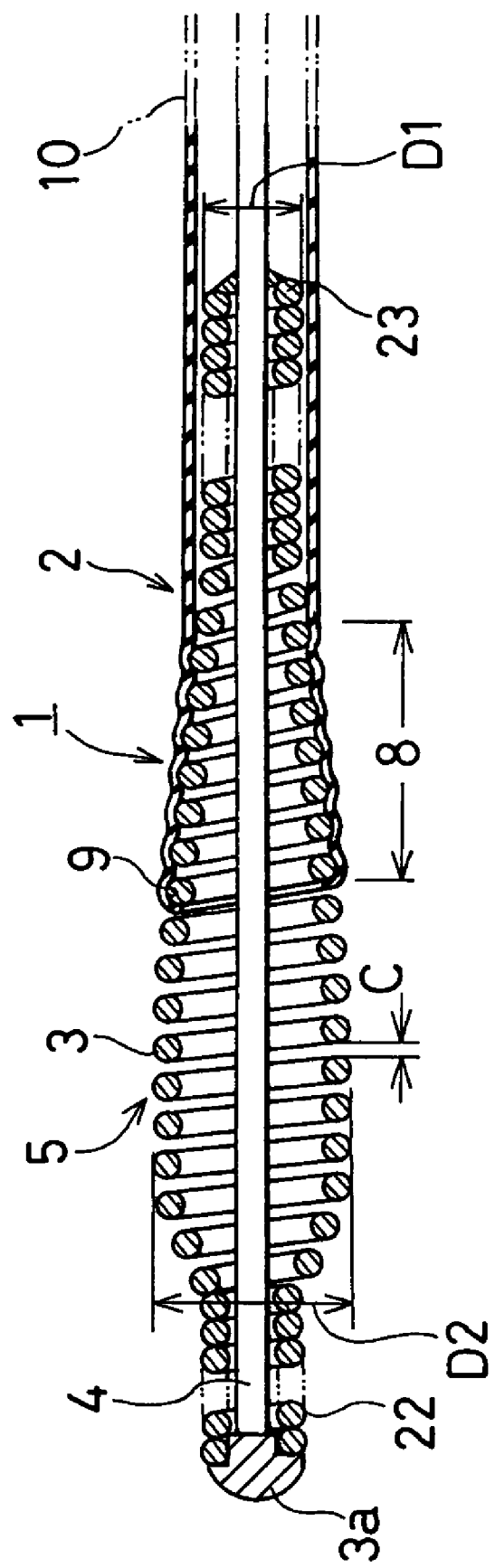
FIG. 10 shows a way how the medical guide wire is introduced into the blood vessel together with the balloon catheter.

FIG. 10 shows a way how the medical guide wire 1 is introduced into the blood vessel together with the balloon catheter 2. In this instance, a forward helical spring 22 and a rearward helical spring 23 are discretely wound around the core member 4. The forward helical spring 22, however, can be consecutively extended to be connected to the rearward helical spring 23.

Figure 11:
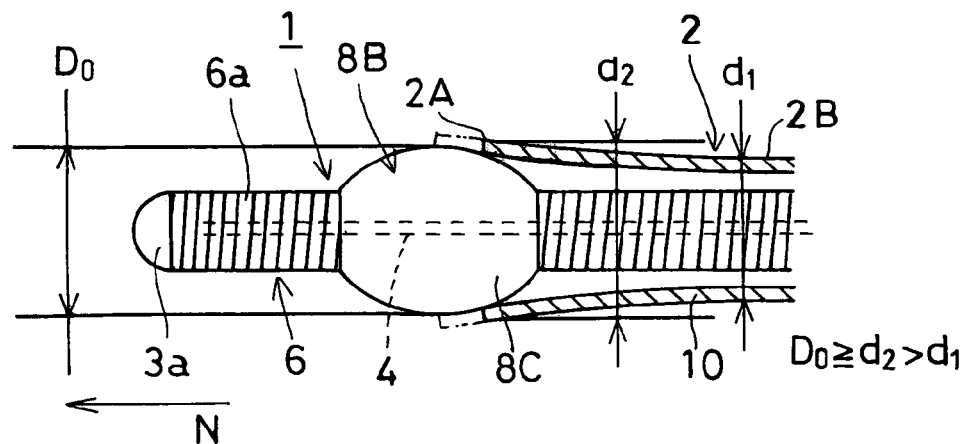
FIG. 11 shows a plan view of a medical guide wire according to a seventh embodiment of the invention.

FIG. 11 shows a way how the medical guide wire 1 and the balloon catheter 2 are introduced into the blood vessel according to a seventh embodiment of the invention. The medical guide wire 1 is firstly introduced into the blood vessel, and then the balloon catheter 2 is inserted into the blood vessel in the direction of an arrow N to fit over the front catheter engagement portion 8B which is mirror-finished in the same manner as done in the fifth embodiment of the invention (FIG. 7).

In this situation, the front catheter engagement portion 8B readily introduces the balloon portion 10 into the strictured area (P) of the blood vessel without injuring the blood vessel and the strictured area (P).

In order to realize this effect, the front catheter engagement portion 8B has a rear end 8C which is provisionally connected to a front end 2A of the balloon catheter 2. The front catheter engagement portion 8B is formed from a mirror-finished barrel portion, to which the balloon catheter 2 is connected at the time when inserted into a coronary artery concurrently with the guide wire 1.

In this instance, it is to be noted that the mirror-finished barrel portion may be also formed into a spindle-shaped configuration. The front catheter engagement portion 8B may be mirror-finished only at a portion to which a flared end portion of the balloon catheter 2 is connected as described hereinafter.

The front catheter engagement portion 8B defines an entirely mirrored surface and represented by the mirror-finished barrel portion is integrally formed by soldering the helical spring 6 and the core member 4 in one piece. A front end 2A of the balloon catheter 2 is diametrically smaller than a maximum diameter ($D_o$) of the front catheter engagement portion 8B, and elastically deforms to be diametrically greater than a tube portion except for the front end 2A of the balloon catheter 2. The elastically deformed front end 2A serves as the flared end portion when the front end 2A of the balloon catheter 2 engages with the rear end 8C of the front catheter engagement portion 8B. A diameter (d2) of the flared end portion becomes greater than a diameter (d1) of the tube portion except for the front end 2A of the balloon catheter 2.

Figure 12:
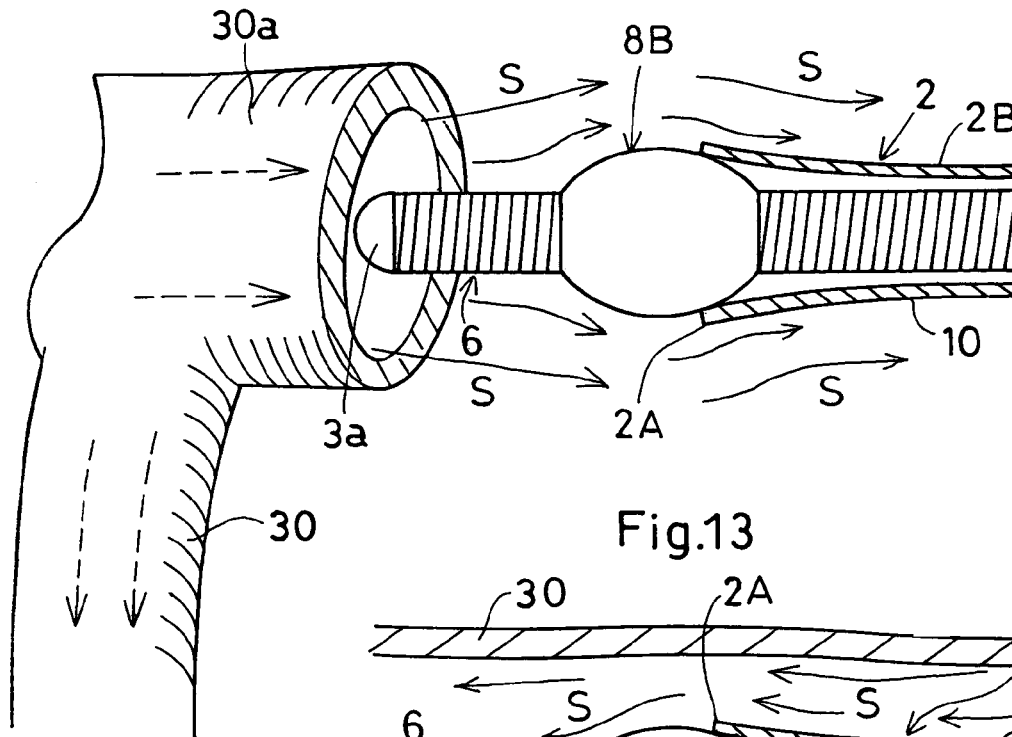
FIGS. 12 and 13 show schematic views of the guide wire navigating into the coronary artery.

Upon concurrently inserting the guide wire 1 and the balloon catheter 2 into the blood vessel until the guide wire 1 reaches an entrance 30a of the coronary artery 30 as shown in FIG. 12, the guide wire 1 is subjected to a reverse pressure from the blood stream S. In the meanwhile, the guide wire 1 is subjected to a forward pressure from the blood stream S once entered into the coronary artery 30.

Thus, the forward propelling force is established to readily make the guide wire 1 insertable into the strictured area (P) in the deep and sinuous thin blood vessels.

From the reason that the guide wire 1 moves forward against the blood streams S (see FIG. 12) from the aorta through the aorta arch to the entrance 30a of the coronary artery 30, the following advantages are obtained.

The mirror-finished barrel portion forms a streamlined flush surface similar to a fusiform surface, the structure is likely subjected to a low resistance drag from the blood streams S due to its low drag coefficient.

The front catheter engagement portion 8B which serves as a mirror-finished barrel portion reduces a friction drag against the blood streams S so as to prevent the thrombosis from depositing on the mirror-finished barrel portion.

When the front end 2A of the balloon catheter 2 diametrically exceeds the maximum diameter ($D_o$) of the front catheter engagement portion 8B, a sectional area increases to which the balloon catheter 2 is subjected from the blood streams S. When the front end 2A of the balloon catheter 2 is diametrically smaller than the maximum diameter ($D_o$) of the front catheter engagement portion 8B, the drag resistance to which the balloon catheter 2 is subjected, is generally equal to the drag resistance to which the front catheter engagement portion 8B is subjected from the blood streams S.

Figure 13:
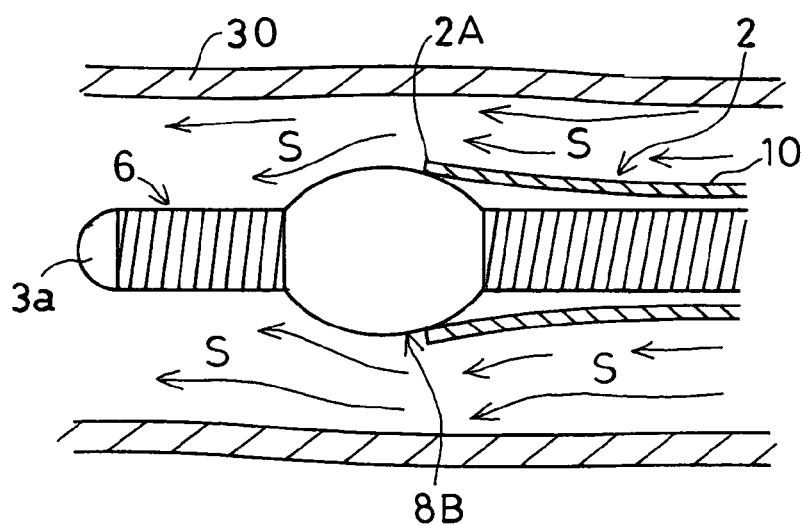

Within the coronary artery 30, the balloon catheter 2 moves forward together with the front catheter engagement portion 8B in such a direction as the blood streams S flow as shown in FIG. 13. For this reason, the blood streams S flow in parallel along the outer surface of the tube portion 2B except for the front end 2A of the balloon catheter 2. The blood streams S disperse at the flared end portion 2A of the balloon catheter 2 to give a reaction force to the flared end portion 2A so as to help propel the balloon catheter 2 forward.

Due to the reason that the tube portion 2B except for the front end 2A of the balloon catheter 2 is neither flared not mirror-finished, the drag resistance increases between the tube portion 2B and the blood streams S. This also adds a reaction force to the balloon catheter 2 to help it propel forward.

With the front catheter engagement portion 8B partly covered by the flared end portion 2A, the non-mirror-finished tube portion of the balloon catheter 2 increases the friction drag. With the increased friction drag, the flared end portion 2A increases the pressure drag to render the balloon catheter 2 deeply insertable into the blood vessel together with the front catheter engagement portion 8B.

In general, the tubular balloon is manufactured by means of an extrusion process with the use of metallic mold such as a dice, a nipple or the like. For this reason, an inner surface of the metallic mold is as smooth as a mirror-finished surface. The subject concept is to make the mirror-finished surface of the front catheter engagement portion 8B engage with the smooth inner surface of the tubular balloon so as to increase the drag coefficient, thus producing the physical absorbable attraction between the front catheter engagement portion 8B and the flared end portion 2A of the balloon catheter 2 to act as the provisionally connecting means.

Namely, the subject concept is that the provisionally connecting means makes it easier to perform the connection and detachment (disconnection) between the front catheter engagement portion 8B and the balloon catheter 2.

An engagement force achieved between the front catheter engagement portion 8B and the balloon catheter 2 is explained with the following factors taken into consideration.

First is the physical absorption between the mirror-finished surface of the barrel portion and the inner smooth surface of the balloon tube 10.

Second is a mechanical engagement produced as a contraction force reactive to an expansible force of the front end tube of the balloon catheter 2.

Figure 14:
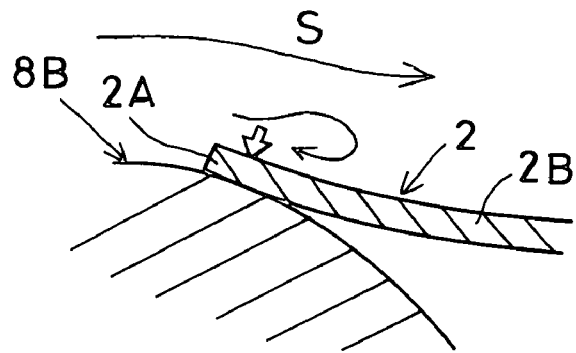
FIG. 14 shows a flared end portion absorbably engaging with the front catheter engagement portion.
Figure 15:
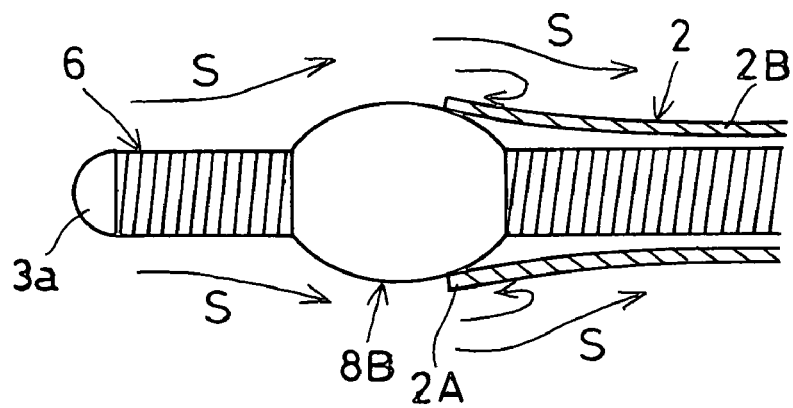
FIGS. 15 and 16 show schematic views of the guide wire navigating against blood streams.
Figure 16:
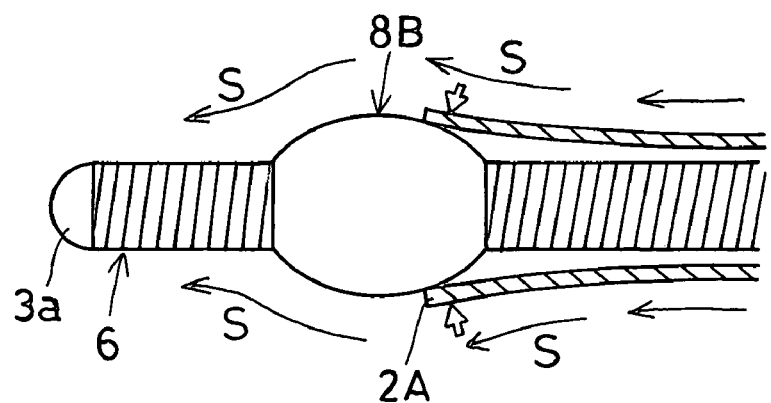

Third is an attachment action produced with the blood stream direction taken into account. That is an auxiliary attachment force produced by rotational flows reversal to the blood stream direction kept until reaching the entrance of the coronary artery 30. Within the coronary artery 30, another attachment action applied by pushing the flared front end portion 2A due to the blood streams S as shown in FIGS. 14, 15 and 16.

The detachment force is produced by considering as an opposite action of the above matter. When the barrel portion is entirely covered by the front end tube 2A of the balloon catheter 2, it becomes difficult to detach the barrel portion 8B from the front end tube 2A of the balloon catheter 2.

In particular, the very thin wire is used for the guide wire (helical spring) to make it highly flexible with less rigidity. This readily makes the very thin wire deform (buckled) within the front end tube, thus making it more difficult to detach the guide wire from the barrel portion. This is true with the case when the the front end tube of the balloon catheter 2 coveres more than half of the barrel portion extending beyond its maximum diameter section.

Figure 17:
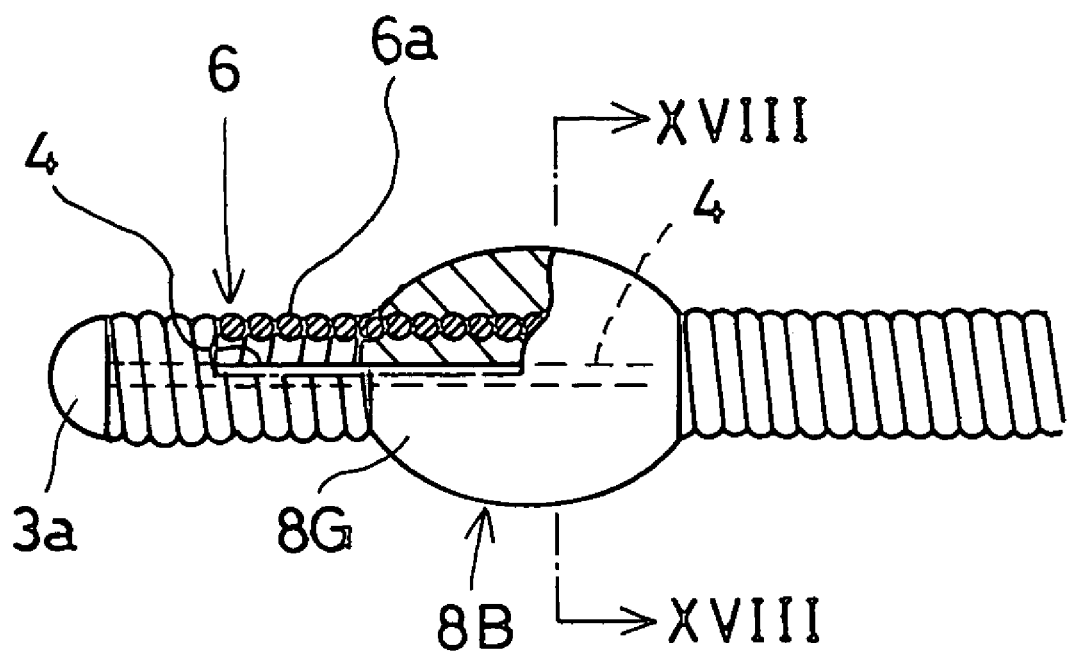
FIG. 17 shows a plan view of the medical guide wire in which a barrel portion is soldered to a helical spring.
Figure 18:
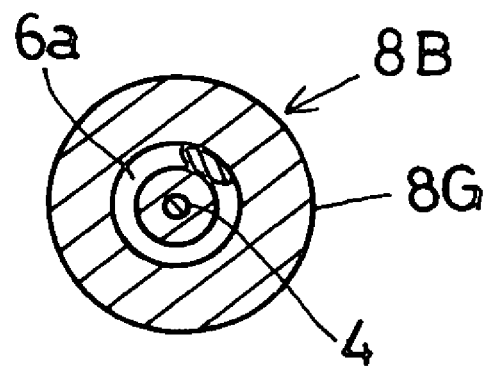
FIG. 18 shows a latitudinal cross sectional view of of the medical guide wire taken along the line XVIII—XVIII of FIG. 17.

Concerning to the soldering portion 8G fixdedly provided on the helical spring 6, the soldering portion 8G is buffed up to render the mirror-finished barrel portion into a spindle-like configuration as shown in FIGS. 17 and 18.

Due to the soldering portion 8G fixedly securing the helical line elements 6a to the elogantion core 4, these three sections are strongly connected to form the solidly integrated barrel portion structure. The soldering portion 8G can be secured at any place as desired, regardless of the length and position of the helical coil spring 6.

It is to be noted that with the use of silver or gold solder metal as radiopaque material, it is possible to function it as a marker.

The mirror-finished treatment is provided on the barrel portion to decrease its contact angle against the liquid phase because the soldering metal has a low wettability. The mirror-finished treatment decreases a surface tension energy to suppress the thrombosis formation and deposit.

The decrease of the contact angle against the liquid phase insures a good wetting relationship with the liquid so as to attain a tightness between the mirror-finished barrel portion and the flared end 2A of the front catheter engagement portion 8B, thus strengthening a physical absorption to increase an adherence toward the mirror-finished barrel portion under the Van del Waals' force.

Due to the tightness caused from the physical absorption, the balloon catheter 2 is kept stuck to the mirror-finished barrel portion without detaching from it even when manipulatively pulled lightly, although a suction pressure is slightly lost between the mirror-finished barrel portion and the flared end 2A of the balloon catheter 2.

Generally, an adhesion force grows at an interface between mirrored surfaces engaged so as to increase a friction therebetween. This analogy can be applied to the interface between the mirror-finished barrel portion and the flared end 2A of the balloon catheter 2 as an example to increase the physical absorption therebetween.

When a coefficient of the friction ($\mu$) is expressed by the formula as $\mu = S1/H$, where S1 is a force applied per unit area and H represents a hardness. From the formula, the friction ($\mu$) is not influenced by a surface roughness, however the friction ($\mu$) changes depending on the surface roughness. This reality explains the theory that the friction ($\mu$) increases because the adhesion force grows.

Figure 19:
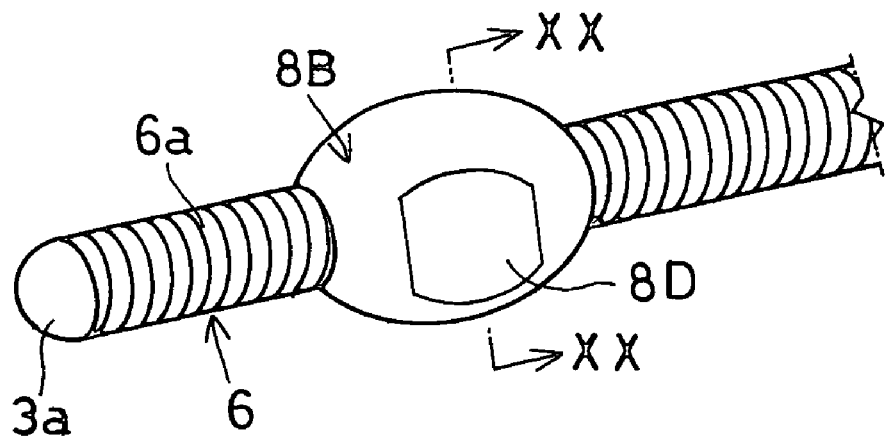
FIG. 19 shows a perspective view of the medical guide wire according to an eighth embodiment of the invention.
Figure 20:
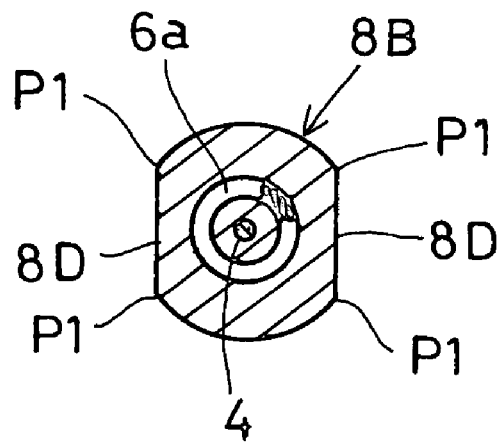
FIG. 20 shows a latitudinal cross sectional view of of the medical guide wire taken along the line XX—XX of FIG. 19.

As an eighth embodiment of the invention, both lengthwise sides of the front catheter engagement portion 8B are undercut to parallel flat sections 8D as shown in FIGS. 19 and 20.

The following are reasons why the provisionally connecting means is arranged so that both lengthwise sides of the mirror-finished barrel portion are undercut to form parallel flat sections 8D. This notion includes the physical absorption by the mirror-finish surface and a mechanical engagement attachment. The latter mechanical engagement attachment becomes stronger in the mirror-finished barrel portion at is outer surface than the one circular in cross section. This is because the circumferential length becomes greater to increase the mechanical engagement attachment when the cross sectional area of both the former and latter is the same.

Moreover, upon connecting the mirror-finished barrel portion and the front end tube 2B of the balloon catheter 2, the mirror-finished barrel portion imparts a high stress to the front end tube 2B at cornered points P1 as shown in FIG. 13. For this reason the front end tube 2B is bent at the cornered points P1, and forcibly deformed in a tensile direction to enhance a contraction force.

As understood from the foregoing description, the medical guide wire and the balloon catheter are inserted into the blood vessel with one single step procedure upon placing the balloon portion at the strictured area of the blood vessel. This enables the manipulator to quickly placing the balloon portion at the strictured area of the blood vessel with ease and safe, thus alleviating pains the patient suffers at the time of inserting the medical guide wire into the blood vessel to cure the strictured area without injuring the blood vessel and the strictured area of the blood vessel.

It is observed that the carves 12 may be provided with the balloon catheter 2 in the second and third embodiments of the invention (FIGS. 2 and 3).

While there has been described what is at present thought to be preferred embodiments of the invention, it will be understood that modifications may be made therein and it is intended to cover in the appended claims all such modifications which fall within the scope of the invention.

What is claimed is:

1. A medical device including a guide wire and a tubular balloon catheter in which the guide wire and the catheter are engaged and inserted into a coronary artery comprising:

a front end having a front catheter engagement portion that is provisionally connected to a front end of the balloon catheter as a provisionally connecting means, the front catheter engagement portion is formed from a mirror-finished barrel portion to have an entirely mirrored surface, and the provisionally connected balloon catheter is inserted into a coronary artery concurrently with the guide wire, wherein the mirror-finished barrel portion is formed by providing a soldering portion integrally fixed in one piece on a helical spring portion of the guide wire and a core inserted into the guide wire;

a front end of the balloon catheter is diametrically smaller than a maximum diameter of the mirror-finished barrel portion, and elastically deforms to be diametrically greater than a tube portion of the balloon catheter so as to form a flared end portion when the mirror-finished barrel portion absorbably engages with the front end of the balloon catheter due to a physical adhesion at the time of provisionally connecting the balloon catheter; and wherein both lengthwise sides of the mirror-finished barrel portion form parallel flat sections.

2. The medical device according to claim 1, wherein the parallel flat sections are cut at its outer surface.

* * * * *